United States Patent [19]

Berthold

[11] Patent Number: 4,515,940

[45] Date of Patent: May 7, 1985

[54] PROCESS FOR THE PREPARATION OF ARYLDIAZOSULFONATES

[75] Inventor: Rüdiger Berthold, Bad Soden am Taunus, Fed. Rep. of Germany

[73] Assignee: Hoechst Aktiengesellschaft, Frankfurt, Fed. Rep. of Germany

[21] Appl. No.: 391,855

[22] Filed: Jun. 24, 1982

[30] Foreign Application Priority Data

Jun. 26, 1981 [DE] Fed. Rep. of Germany ....... 3125104

[51] Int. Cl.$^3$ ............................................. C07C 113/04
[52] U.S. Cl. .................................... 534/565; 534/558; 534/560; 534/556
[58] Field of Search ..................................... 260/141 P

[56] References Cited

U.S. PATENT DOCUMENTS

| | | | |
|---|---|---|---|
| 1,897,410 | 2/1933 | Zitscher et al. | 260/141 |
| 1,975,409 | 10/1934 | Schnitzpahn et al. | 260/141 |
| 3,117,954 | 1/1964 | Hupfer | 260/141 |

OTHER PUBLICATIONS

Chemische Berichte, vol. 92, No. 12, (1959), pp. 3031–2043, Lewis et al.

Houben–Weyl, "Methoden der Organischen Chemie", 4 edition, vol. X/3, Part 3, (1956), Georg Thieme Verlag, Stuttgart, pp. 570–576.

Ullmanns Encyklopadie der technischen Chemie, 4 edition, vol. 10, (1975), Verlag Chemie, Weinheim, p. 118.

*Primary Examiner*—Floyd D. Higel
*Attorney, Agent, or Firm*—Curtis, Morris & Safford

[57] ABSTRACT

The invention relates to a process for the preparation of aryldiazosulfonates by reacting aqueous solutions of aryldiazonium salts with solutions or suspensions of sulfites, in particular in a manner such that the presence of an excess of one of the two reactants during the reaction is substantially excluded. The process according to the invention makes it possible substantially to increase the yields of aryldiazosulfonates.

10 Claims, No Drawings

PROCESS FOR THE PREPARATION OF ARYLDIAZOSULFONATES

Methoden der Organischen Chemie (HOUBEN-WEYL) Vol.X/3, "Stickstoffverbindungen (Nitrogen Compounds) I, Part 3", Stuttgart 1965, pages 570-576, discloses processes for the preparation of aryldiazosulfonates, in which aryldiazonium salt solutions are allowed to flow, with stirring and cooling, into an alkali metal sulfite solution to which an alkali metal carbonate or bicarbonate has been added to neutralize the excess acid used for the diazotization. Times of up to two hours are given as the influx times of the diazonium salt solutions (example from page 575 of the above publication). Ullmanns Encyclopädie der technischen Chemie, 4th edition, Volume 10, Weinheim 1975, page 118, top right column, also mentions an addition of the diazonium salt solution "in the course of several hours".

Even when the process is extrapolated to the industrial scale, feed times of ½ to 1 hour result from time to time, depending on the amount to be reacted and on the diameter of the feed pipe. As a result of these feed times, a large amount of excess sulfite is present at times in the reaction vessel, in addition to the diazosulfonates.

When these processes are repeated using variously substituted aryldiazonium salts, very variable yields of between 40 and 85% of theory are obtained. For example, p-chlorobenzenediazonium chloride gives 43%, m-chlorobenzenediazonium chloride gives 36%, m-toluenediazonium chloride gives 69%, o-chlorobenzenediazonium chloride gives 36%, p-dimethylaminobenzenediazonium chloride gives 54%, p-carbamoylbenzenediazonium chloride gives 58%, benzenediazonium chloride gives 72%, p-methoxybenzenediazonium chloride gives 80% and p-sulfobenzenediazonium chloride gives 10 to 20% of the corresponding diazosulfonate.

It has now been found that the yields of aryldiazosulfonates can be substantially increased when care is taken to ensure that, as far as possible, none of the reactants is present in excess during the reaction.

The invention therefore relates to a process for the preparation of compounds of the general formula I $$R_nAr-N=N-SO_3M \quad (I)$$

in which Ar represents an aromatic isocyclic structure or heterocyclic structure, R are identical or different and represent alkyl, aryl, amino, hydroxyl, alkoxy, aryloxy, halogen, nitro, acylamino, carbamoyl, alkylcarbamoyl, arylcarbamoyl, dialkylamino, arylamino, sulfo or sulfamoyl, M represents hydrogen, an alkali metal or one equivalent of an alkaline earth metal, and n represents 0 or an integer from 1 to 5, by reacting aqueous solutions of diazonium salts of the formula II $$(R_nAr-N=N)^+Z^- \quad (II)$$

in which Ar, R and n have the abovementioned meanings, and $Z^-$ represents one equivalent of an anion, with solutions or suspensions of alkali metal sulfites or alkaline earth metal sulfites, which comprises substantially excluding the presence of an excess of one of the two reactants during the reaction.

In a preferred embodiment of the invention, Ar represents phenyl, R represents lower alkyl, lower alkoxy, chlorine, bromine, nitro, aryl, amino, acylamino, lower dialkylamino, arylamino, sulfo, sulfamoyl or carbamoyl, M represents an alkali metal, and n represents 0 to 3.

The diazonium salt solutions are prepared according to known methods, by diazotizing aromatic amines.

Examples of suitable amines are aniline, o-chloroaniline, m-chloroaniline, p-chloroaniline, o-anisidine, m-anisidine, p-anisidine, o-nitroaniline, m-nitroaniline, p-nitroaniline, 2-aminobenzenesulfonic acid, 3-aminobenzenesulfonic acid, 4-aminobenzenesulfonic acid, 5-aminobenzimidazolone, 1-amino-4-chloro-2,5-dimethoxybenzene, o-phenetidine, m-phenetidine, p-phenetidine, p-carbamoylaniline, 3,5-dichloroaniline, o-toluidine, m-toluidine, p-toluidine, 3,5-dimethylaniline, 2,6-dimethylaniline, N,N-dimethylphenylenediamine, phenylenediamine, o-bromoaniline, m-bromoaniline, p-bromoaniline, 4-aminobenzenesulfonamide, α-naphthylamine and 1-amino-4-phenylaminobenzene.

Examples of suitable sulfites are sodium sulfite or potassium sulfite.

The neutralization of the excess acid in order to obtain the pH range of 7 to 13 which is optimum for the reaction can be effected by the addition of, for example, sodium carbonate, sodium bicarbonate or potassium carbonate. Advantageously, these neutralizing agents are added to the sulfite solution.

The presence of an excess of one of the two reactants is substantially prevented by throwing the diazonium salt solution into the very rapidly stirred sulfite solution. In general, the aryldiazosulfonate is precipitated immediately, and a more or less thick suspension is formed, particularly after the rearrangement of the syn-form to the anti-form. In order to achieve complete reaction of the diazonium salt with the sulfite under these conditions, the choice of the mixing unit must be adapted to the consistency of the reaction mixture. In many cases, however, it is also possible, by adding a wetting agent, to prevent the reaction suspension from becoming thick. This produces the advantageous result that the suspension remains stirrable in relatively small volumes.

When the process according to the invention is extrapolated to the industrial scale, an excess of one of the two reactants is prevented by adding the diazonium salt solution in each case as rapidly as is technically possible to the very rapidly stirred solution or suspension of the sulfite. Particularly advantageously, equivalent amounts of diazonium salt solution and sulfite solution are pumped into a mixing unit. This may also be carried out continuously, for example by metering stoichiometric amounts of the solutions or suspensions of the reactants continuously into a flow mixer, and then passing the mixture into a stirrable retention tank.

The diazonium salt solution and sulfite solution can be combined at temperatures from $-20°$ C. to $120°$ C. Preferred temperature ranges are $+5°$ C. to $60°$ C., in particular $+5°$ C. to $30°$ C. The reaction is advantageously carried out at a pH value of 7 to 13; the preferred pH range is 8 to 10.

Aryldiazosulfonates are intermediates for the preparation of arylhydrazines. If, for process reasons, these compounds have to be isolated, or if the stage of the aryldiazosulfonate, without being isolated, is further reduced to the hydrazo stage in a one-pot process, using reducing agents other than sodium bisulfite, the increases in yield, which are obtained using the process described and which are very large in some cases, improve the cost-efficiency.

In the examples which follow, parts and percentages relate to weight.

EXAMPLE 1

93 parts of aniline were dissolved in a mixture of 238 parts of 31% strength hydrochloric acid and 100 parts of water, and were diazotized in a known manner with 172 parts of 40% strength sodium nitrite solution.

The diazonium chloride solution thus obtained, which contained hardly any free acid and was at about −5° C., was thrown into a freshly prepared mixture of 273 parts of 40% strength sodium bisulfite solution, 127.5 parts of 33% strength sodium hydroxide solution, 100 parts of water and 10 parts of sodium carbonate, while stirring vigorously. An orange-red solution was formed which remained clear for a few seconds until the yellow diazosulfonate was precipitated. Frequently, after only a few minutes, a thick slurry was formed which was hardly stirrable anymore, but which soon disintegrated after the addition of a wetting agent. If the wetting agent was added at the outset, the precipitate remained readily stirrable. The mixture was stirred for a further 2 to 3 hours to complete the rearrangement of the syn-form to the anti-form, and the precipitate was then filtered off under suction.

187 parts of sodium benzenediazosulfonate (90% of theory) were obtained in this manner.

EXAMPLES 2 TO 18

The diazosulfonates in the table below were prepared analogously to Example 1. Owing to the poor solubility of many arylamine hydrochlorides or even the diazonium salts, it was not possible to allow the liquid volume to fall below a certain volume during diazotization. The amount of water and the amount of hydrochloric acid were proportioned such that a diazonium salt solution was formed which was as concentrated as possible and which contained only a very small excess of hydrochloric acid. In some cases, in which an acid excess greater than that given above was required during the diazotization, the addition of sodium carbonate had to be increased correspondingly.

The temperature of the diazonium salt solutions was from −20° to +60° C., depending on their particular thermal stability.

Sometimes, for example in the case of p-nitrobenzenediazosulfonate, it was advantageous if stirring was continued for a relatively long time (15 hours). Owing to the large volume of reaction mixture which may be required, some diazosulfonates, for example sodium 2,6-dimethylbenzenediazosulfonate, crystallized out only after the reaction solution had been concentrated in a water jet vacuum. To improve the yield, a further precipitate of aryldiazosulfonate was obtained in most cases by salting out the mother liquor. If the consistency of the main precipitate permitted, the calculated amount of sodium chloride could already be added to it.

| Example | Diazosulfonate | Yield |
| --- | --- | --- |
| 2 | Cl—⟨⟩—N=N—SO₃Na | 81% |
| 3 | CH₃O—⟨⟩—N=N—SO₃Na | 94% |
| 4 | O₂N—⟨⟩—N=N—SO₃Na | 81% |
| 5 | NaSO₃—⟨⟩—N=N—SO₃Na | 92.7% |
| 6 | O=C(NH)(NH)—⟨⟩—N=N—SO₃Na | 83% |
| 7 | Cl—⟨⟩(OCH₃)(OCH₃)—N=N—SO₃Na | 94% |
| 8 | C₂H₅O—⟨⟩—N=N—SO₃Na | 91% |
| 9 | H₂NOC—⟨⟩—N=N—SO₃Na | 97% |
| 10 | ⟨⟩(Cl)—N=N—SO₃Na | 77% |
| 11 | ⟨⟩(Cl)—N=N—SO₃Na | 69% |
| 12 | ⟨⟩(Cl)(Cl)—N=N—SO₃Na | 70% |
| 13 | CH₃—⟨⟩—N=N—SO₃Na | 90% |
| 14 | ⟨⟩(CH₃)—N=N—SO₃Na | 85% |
| 15 | ⟨⟩(CH₃)(CH₃)—N=N—SO₃Na | 80% |
| 16 | ⟨⟩(CH₃)(CH₃)—N=N—SO₃Na | 95% |
| 17 | (CH₃)₂N—⟨⟩—N=N—SO₃Na | 87% |
| 18 | H₂N—⟨⟩—N=N—SO₃Na | 75% |

EXAMPLE 19

An aryldiazonium chloride solution prepared continuously according to U.S. Pat. No. 3,423,391 and a solution containing sodium bisulfite, sodium hydroxide solution, water and sodium carbonate according to the composition given in Example 1 were pumped simultaneously into a flow mixer so that neither of the two solutions was present in excess. The reaction solution leaving the mixer passed into a stirrable retention tank, from which point it could be processed further.

EXAMPLE 20

Commercially available diazo salts are also suitable for the reaction with sodium sulfite:

232 parts of p-phenylaminobenzenediazonium chloride (calculated for 100% strength) were dissolved in 1,200 parts of water at 53° C. The clarified solution was thrown into a solution of 132 parts of sodium sulfite and 10 parts of sodium carbonate in 500 parts of water, while stirring thoroughly. The mixture was stirred for a further 3 hours and was salted out with 350 parts of sodium chloride, and the precipitated diazosulfonate was filtered off under suction at 5° C. 392 parts of dry sodium p-phenylaminobenzenediazosulfonate containing sodium chloride was obtained in this manner. Purity 74%, corresponding to 290 parts of 100% strength product. This is 97% of theory.

I claim:

1. A process for the preparation of a compound of the formula I

    (I)

in which Ar represents an aromatic isocyclic structure or heterocyclic structure, R are identical or different and represent alkyl, aryl, amino, hydroxyl, alkoxy, aryloxy, halogen, nitro, acylamino, carbamoyl, alkylcarbamoyl, arylcarbamoyl, dialkylamino, arylamino, sulfo or sulfamoyl, M represents hydrogen, an alkali metal or one equivalent of an alkaline earth metal, and n represents 0 or an integer from 1 to 5, by reacting an aqueous solution of the diazonium salt of the formula II

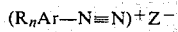    (II)

in which Ar, R and n have the abovementioned meanings and $Z^-$ represents one equivalent of an anion, with a solution or suspension of an alkali metal sulfite or alkaline earth metal sulfite, which comprises substantially excluding the presence of an excess of one of the two reactants during the reaction and wherein the diazonium salt solution is added as rapidly as is technically possible to the very rapidly stirred solution or suspension of the sulfite.

2. The process as claimed in claim 1, wherein Ar represents phenyl, R represents lower alkyl, lower alkoxy, chlorine, bromine, nitro, aryl, amino, acylamino, lower dialkylamino, arylamino, sulfo, sulfamoyl or carbamoyl, M represents an alkali metal, and n represents 0 to 3.

3. The process as claimed in claims 1 and 2, wherein stoichiometric amounts of the solutions or suspensions of the reactants are metered continuously into a flow mixer, and the mixture is then passed into a stirrable retention tank.

4. The process as claimed in claim 1, wherein a wetting agent is added.

5. The process as claimed in claim 1, wherein the reaction is carried out at −20° to +120° C.

6. The process as claimed in claim 1, wherein the reaction is carried out at 5° to 60° C.

7. The process as claimed in claim 1, wherein the reaction is carried out at 5° to 30° C.

8. The process as claimed in claim 1, wherein the reaction is carried out at pH of 7 to 13.

9. The process as claimed in claim 1, wherein the reaction is carried out at a pH of 8 to 10.

10. The process as claimed in claim 1, wherein none of the two reactants are present in excess during the reaction.

* * * * *